United States Patent [19]

Dauben et al.

[11] 4,277,604
[45] Jul. 7, 1981

[54] FACILE SYNTHESIS OF CODEINE PRECURSORS FROM THEBAINE

[75] Inventors: William G. Dauben, Berkeley, Calif.; Craig P. Baskin, Avenel, N.J.; Herman C. H. A. vanRiel, Alphen aan den Rijn, Netherlands

[73] Assignee: The United States of America as represented by the Department of Health and Human Services, Washington, D.C.

[21] Appl. No.: 115,411

[22] Filed: Jan. 25, 1980

[51] Int. Cl.$^3$ .......................................... C07D 489/02
[52] U.S. Cl. ........................................ 546/44; 546/45
[58] Field of Search .................................. 546/44, 45

[56] References Cited

U.S. PATENT DOCUMENTS

| | | | |
|---|---|---|---|
| 3,112,323 | 11/1963 | Krausz | 546/45 |
| 4,054,566 | 10/1977 | Rapoport et al. | 546/45 |
| 4,110,329 | 8/1978 | Rapoport et al. | 546/44 X |

OTHER PUBLICATIONS

Gavard, et al., Bull. Soc. Chim. France, (1965), pp. 486–490.
Barber, et al., J. Med. Chem., vol. 19, No. 10, pp. 1175–1180, (1976).
Samchenko, et al., Chemical Abstracts, vol. 69, 85862e, (1968).

Primary Examiner—Anton H. Satto
Assistant Examiner—Diana G. Rivers
Attorney, Agent, or Firm—John S. Roberts, Jr.

[57] ABSTRACT

Thebaine is converted to a mixture of codeinone and neopinone in aqueous formic acid solution containing as catalyst a mercuric salt. Thebaine is converted to a neopinone ketal by irradiation in an alkanol or to a mixture of neopinone and codeinone in an acidic aqueous solution. Neopinone ketals, codeinone and neopinone can be converted to codeine.

7 Claims, No Drawings

FACILE SYNTHESIS OF CODEINE PRECURSORS FROM THEBAINE

The invention described herein was made in the course of work under a grant or award from the Department of Health, Education and Welfare.

BACKGROUND OF THE INVENTION

1. Field of the Invention

This invention is directed to synthesis, starting from thebaine, of neopinone dialkyl ketals, neopinone or codeinone, each of which is convertible to codeine by conventional processes.

2. Description of Prior Art

Codeine, widely used as a pain-killer and cough suppressant, has conventionally been prepared by methylation of morphine, which is also traditionally used as the raw material for the illicit drug heroin. Morphine is obtained by extraction of opium or poppy straw from the opium poppy (*Papaver somniferum*), of which commercial cultivation is illegal in the United States. Because no commercially viable total synthesis of codeine has been devised and because of the uncertainties of relying on foreign sources of intermediates for codeine, it is apparent that development of alternative routes to codeine using domestically available non-addictive intermediates is of considerable significance.

Thebaine, a product isolated from the perennial poppy *P. bracteatum*, which does not produce morphine, would be an acceptable alternative to morphine as an intermediate for codeine. An additional advantage of using thebaine as an intermediate is that thebaine is not readily converted to morphine and thence to heroin. Moreover, the cultivation of *P. bracteatum* is not proscribed.

Krausz, in U.S. Pat. No. 3,112,323, and Gavard et al., *Bull. Soc. Chim.* France (1965) at 486–490, have described the conversion of thebaine (1) to codeine by treatment with anhydrous HBr to produce a product which is dehydrobromated to a mixture containing codeinone (4), reduction of which gives codeine (6).

Rapoport et al., in U.S. Pat. Nos. 4,054,566 and 4,110,329, and Barber et al., *J. Med. Chem.*, vol. 19 (1976) at 1175–1180, describe the conversion of thebaine (1) to a mercurated neopinone dimethyl ketal (3, R is $CH_3$), which can be hydrolyzed by formic acid to a mixture of codeinone (4) and neopinone (5), which mixture can be converted to codeine (2).

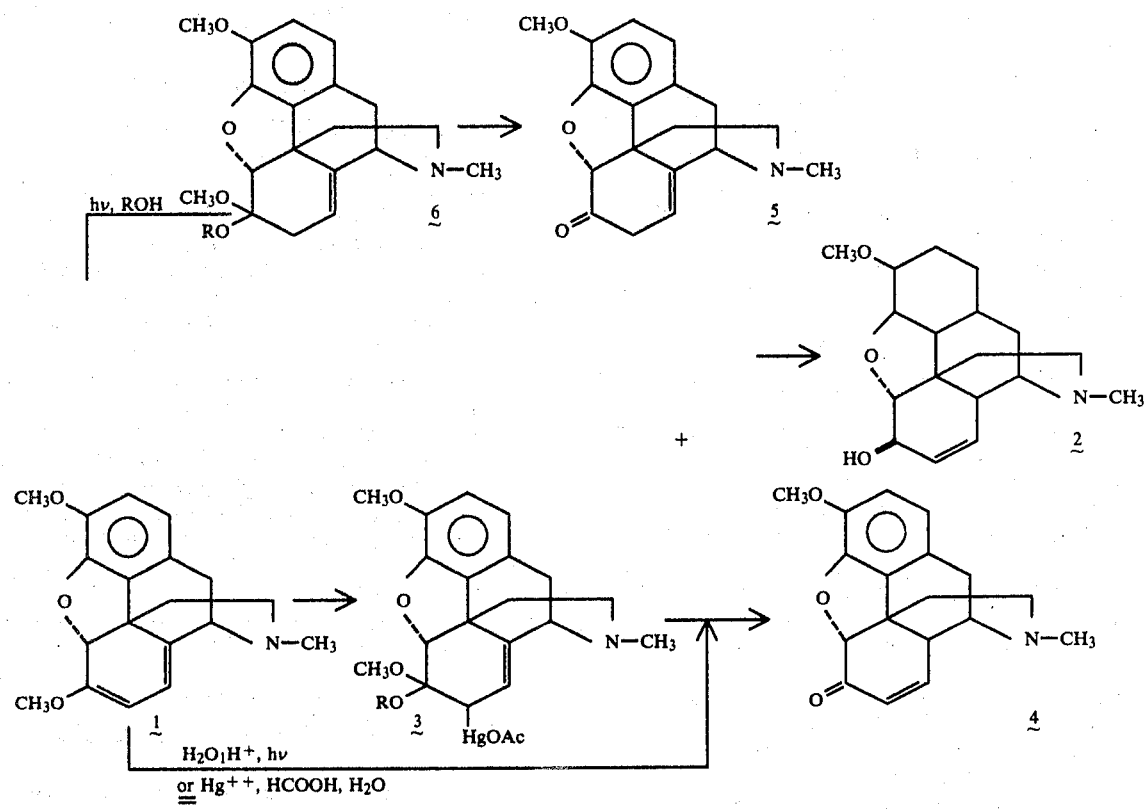

Barber et al., supra, also disclosed that thebaine, treated with an excess of mercuric salt in refluxing aqueous tetrahydrofuran gave a mixture of neopinone and codeinone (1:3 ratio) in 38% yield.

The conversion of thebaine to a mixture of codeinone, neopinone and/or neopinone ketal by mercury-catalyzed or photochemical routes has been disclosed by the applicants, *J. Org. Chem.*, vol. 44 (1979), at 1567–1569, incorporated herein by reference.

SUMMARY OF THE INVENTION

In one aspect, this invention relates to an improvement in a process of converting thebaine (1) to a mixture of codeinone (4) and neopinone (5) in a solvent containing water and a mercuric salt, the improvement comprising use of an aqueous solution up to about 5 N in formic acid and containing 0.5–20 molar % of mercuric acetate with respect to thebaine.

In another aspect, this invention relates to a method of converting thebaine (1) to neopinone methyl (alkyl)

ketal (6), codeinone (4) or neopinone (5) by irradiation with ultraviolet light. Reaction done in an alkanol solvent gives the ketal (6), whereas use of an acidic aqueous solution gives the codeinone-neopinone mixture.

DETAILED DESCRIPTION

The product obtained by irradiation of thebaine (1) with ultraviolet light (about 3650 Å) is dependent on the solvent selected. When the reaction is carried out in a lower alkanol, i.e., ROH of 1-4 carbon atoms, the product can be a mixed ketal of formula (6), wherein the structure at $C_6$ is

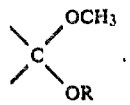

When methanol is employed as solvent, as is preferred, R is methyl and the product is the dimethyl ketal.

In an acidic aqueous solution, irradiation of thebaine produces a mixture of neopinone (5) and codeinone (6), which is predominantly neopinone. The aqueous solution is conveniently acidified with a strong acid, such as HCl, $H_2SO_4$ or $H_3PO_4$, so that the acidity of the reaction mixture is 0.25 N-1.0 N.

Irradiation of s-cis-1,3-dienol ethers such as thebaine had not been investigated previously. However, irradiation of s-trans-dienol ethers, such as 3-methoxycholesta-3,5-diene, was reported to give the $\beta,\gamma$-unsaturated ketal. See Just et al., Can. J. Chem., Vol. 42 (1964) at 79 and Lenzoff et al., ibid. at 2801 and 2919.

Conversion of thebaine to codeinone and neopinone in aqueous formic acid can be achieved using as low as about 0.5 molar % of mercuric salt. Preferably, a greater amount of catalyst is used, up to about 20 molar %. Most preferably the amount of mercuric salt is 5-10 molar %.

Any mercuric salt which has some solubility in aqueous formic acid solution can be used, e.g., the acetate, acetyllide, benzoate, bromate, bromide, carbonate, chlorate, chloride, chromate, cyanide, fluoride, fluorsilicate, iodate, iodide, nitrate, oxalate, oxide sulfate, sulfide, thiocyanate or perchlorate. The chloride, bromide and acetate are preferred. The most preferred catalyst is mercuric acetate.

The concentration of formic acid in the aqueous solution can be up to about 5 N, but concentrations of 2-4 N are preferred. The reaction is done at temperatures below about 50° C., preferably at ambient temperature, at which complete conversion to codeinone and neopinone occurs within a day at preferred catalyst levels. Overall yields of codeine, following conventional reactions for reducing the enone mixture, can be 80% or higher.

An unexpected aspect of the mercury-catalyzed reaction in accordance with the invention is the high yield of codeinone and neopinone obtained in relatively short reaction times compared to the reactions reported by Barber et al., supra.

DESCRIPTION OF MOST PREFERRED EMBODIMENT

Conditions most preferred for mercuric ion-catalyzed conversion of thebaine to codeinone and neopinone are as given above, wherein the aqueous solvent is 2-4 N in formic acid, the mercuric salt is mercuric acetate in an amount of 5-10 molar % and the reaction is carried out near room temperature.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following examples, unless otherwise indicated, all parts and percentages are by weight.

Melting points were determined on a Mel-temp apparatus and are uncorrected. $^1$H-NMR spectra were determined on a Varian Associates T-60 spectrometer. Gas phase chromatographic analyses were performed on a Hewlett-Packard 402 high efficiency gas chromatograph, equipped with a 6'×¼" column packed with 3% OV-225, Chromosorb W, AW DMCS, 100-120 M, at a temperature of 230° C., using a flame ionization detector.

EXAMPLE I

Photochemical Formation of Neopinone Dimethyl Ketal (6)

A solution of 623 mg (2 mmol) of thebaine in 150 ml of methanol, freshly distilled from Mg(OMe)$_2$, was deoxygenated with a stream of dry nitrogen. The deoxygenated solution was irradiated with a Hanovia 450-W lamp through a Corex filter under a stream of nitrogen for 2 hr, at the end of which TLC analysis (silica gel, CHCl$_3$:MeOH, 85:15) showed that all the starting material had been consumed. The solution was evaporated to dryness using a rotary evaporator. The residue was purified by column chromatography (silica gel, CHCl$_3$:MeOH, 94:6) to yield 538 mg (78%) of neopinone dimethyl ketal as a light golden oil. The crude product was distilled in a Kugelrohr still to give 420 mg (61%) of methanol adduct; bp 105°-110° C. (0.02 mm Hg) [lit., Barber, supra, bp 90° (0.01 mm Hg)]; nmr (CHCl$_3$): δ 1.80-2.90 (m, 11 H), 2.93 (s, 3 H), 3.50 (s, 3 H), 3.88 (s, 3 H), 4.65 (s, 1 H), 5.36 (D, d, 1 H, J=6.3 Hz), 6.66 (m, 2 H).

EXAMPLE II

Photochemical Formation of a Neopinone - codeinone Mixture

A suspension of 643 mg (2.07 mmol) of thebaine in 165 ml of water was deoxygenated with a stream of dry nitrogen. To the solution was added 250 ml of 1 N HCl (2.5 mmol). The thebaine hydrochloride which formed slowly dissolved. The solution was irradiated with a Hanovia 450 W-lamp through a corex filter for 2.5 hr, after which TLC analysis (CHCl$_3$:MeOH, 85:15) showed that all the starting material had been consumed. To the aqueous solution was added 1.0 g of anhydrous Na$_2$CO$_3$. The resulting suspension was extracted with CHCl$_3$. The organic extract was washed with water, dried over Na$_2$SO$_4$, and evaporated using a rotary evaporator to yield 500 mg (81%) of a brown oil, which was a 9:1 mixture of neopinone and codeinone (nmr analysis of 5$\beta$-proton, Barber, supra).

EXAMPLE III

Hydrolysis of Photochemically-Produced Neopinone Dimethyl Ketal (6)

A solution of 300 mg (0.875 mmol) of photochemically-formed neopinone dimethyl ketal (6) in 20 ml of 3 N formic acid was stirred under a stream of nitrogen at room temperature for 4 days. To the solution was added 100 ml of saturated aqueous solution of K$_2$CO$_3$. The solution was extracted with CHCl$_3$. The organic extract was washed with water, dried over Na$_2$SO$_4$, and evaporated with a rotary evaporator to yield a 2:1 mixture of starting material and enones 4 and 5.

EXAMPLE IV

Mercury-catalyzed Hydrolysis of Photochemically-produced Neopinone Dimethyl Ketal (6)

(a) The procedure described in Example III was repeated with a solution containing 2 mg (0.006 mmol, 0.7 mol %) of Hg(OAc)$_2$. The product (240 mg) was a 1:5 mixture of starting material and enones; the corrected yield of enones 4 and 5 was 89%.

EXAMPLE V

Mercury-catalyzed Hydrolysis of Thebaine (1)

(a) A solution of 234 mg (0.75 mmol) of thebaine and 31.9 mg (0.1 mmol, 13.3 mol %) of Hg(OAc)$_2$ in 20 ml of 3 N formic acid was stirred, under nitrogen at room temperature for 4 days. The solution was diluted with 100 ml of a saturated aqueous solution of K$_2$CO$_3$ and extracted with CHCl$_3$. The organic layer was washed with water, dried over Na$_2$SO$_4$, and evaporated with a rotary evaporator to give a straw-colored solid in 100% yield. The material was a 3:1 mixture of codeinone (4) and neopinone (5) (nmr analysis of the 5$\beta$-proton and GC chromatography).

(b) Use of the procedure of Example V(a) with amounts of Hg(OAc)$_2$ varying from 0.5-20 mol percent of mercuric acetate resulted in the formation of both enones during the first 24 hour (analyzed by GC chromatography).

(c) In an experiment as in Example V(a) using no Hg(OAc)$_2$, no enones were produced in 5 days.

(d) Addition of 0.8 mol % of Hg(OAc)$_2$ in an experiment otherwise as in Example V(a) resulted in complete conversion of thebaine to enone mixture in 18 days. However, the yield of enones was low (~30%) and by-products were formed.

EXAMPLE VI

Conversion of Thebaine (1) to Codeine (2)

A solution of 1.17 g (3.75 mmol) of thebaine (1) and 79.8 mg (0.25 mmol, 6.7 mol %) of Hg(OAc)$_2$ in 100 ml of 3 N formic acid was stirred, under nitrogen, for 6.5 hr. The solution was diluted with 100 ml of saturated aqueous K$_2$CO$_3$ and extracted with CHCl$_3$. The organic layer was washed with water, dried over Na$_2$SO$_4$, and evaporated in a rotary evaporator.

The residue was dissolved in 5.3 ml of CHCl$_3$ and allowed to react with 5.3 ml of a solution of 1.1 g of hydrogen chloride in 10 ml of ether. A precipitate formed immediately, but the reaction was allowed to continue for 30 min before the reaction mixture was diluted with 2.5 ml of CH$_2$Cl$_2$ and 2.5 ml of the above solution of hydrogen chloride in ether. The reaction was allowed to continue for 15 min more, whereupon 250 ml of cold 0.2 N NaOH solution and 50 ml of CHCl$_3$ were added to the mixture. After separation of the layers, the aqueous layer was reextracted with CHCl$_3$. The combined organic extracts were washed with water, dried over Na$_2$SO$_4$, and evaporated using a rotary evaporator.

To the residue, dissolved in 60 ml of methanol, was added 3.02 g (79 mmol) of NaBH$_4$ in 73 ml of methanol. Under nitrogen, the reduction was allowed to proceed for 15 hr. The resulting solution was concentrated to a volume of 60 ml, diluted with 60 ml of 10% NaOH solution, and heated to reflux. The reaction mixture was further diluted with 50 ml of water and extracted with CHCl$_3$. The organic extract was washed with water, dried over Na$_2$SO$_4$, and evaporated using a rotary evaporator to yield 890 mg (79%) of crude white codeine (2), GC analysis of which indicated 90% purity. The crude product was sublimed (100° C., 0.03 mm Hg) to give codeine in 80% yield, mp 151°-154° C. (lit., Barber, supra, 153°-157° C.). The nmr spectrum was identical to that of a commercial sample of codeine.

Mercury concentration of codeine prepared as above was of the order of 22 ppm, according to atomic absorption determination (Lawrence Berkeley Laboratory).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for converting thebaine to a mixture of codeinone and neopinone in a solvent containing water and in the presence of a mercuric salt, the improvement wherein the solvent is up to about 5 N in formic acid and the amount of mercuric salt is 0.5-20 molar % with respect to thebaine.

2. The process of claim 1, wherein the process is conducted near room temperature.

3. The process of claim 1, wherein the solvent is 2-4 N in formic acid.

4. The process of claim 1, wherein the amount of mercuric salt is 5-10 molar %.

5. The process of claim 1, wherein the mercuric salt is mercuric acetate.

6. The process of claim 1, wherein the solvent is 2-4 N in formic acid, the mercuric salt is mercuric acetate in an amount of 5-10 molar % and the process is conducted near room temperature.

7. The process of claim 1, wherein thus-obtained mixture of codeinone and neopinone is further converted to codeine.

* * * * *